(12) United States Patent
Bond-Thorley (10) Patent No.: US 8,578,779 B2
(45) Date of Patent: Nov. 12, 2013

(54) INSPECTION DEVICE

(75) Inventor: Andrew Bond-Thorley, Stone House (GB)

(73) Assignee: Airbus Operations Limited, Bristol (GB)

( * ) Notice: Subject to any disclaimer, the term of this patent is extended or adjusted under 35 U.S.C. 154(b) by 373 days.

(21) Appl. No.: 12/737,402

(22) PCT Filed: Jul. 24, 2008

(86) PCT No.: PCT/GB2008/050622
§ 371 (c)(1),
(2), (4) Date: Jan. 10, 2011

(87) PCT Pub. No.: WO2010/010316
PCT Pub. Date: Jan. 28, 2010

(65) Prior Publication Data
US 2011/0100128 A1    May 5, 2011

(51) Int. Cl.
*G01N 29/00* (2006.01)
*G01N 29/28* (2006.01)

(52) U.S. Cl.
USPC .................................. 73/618; 73/620; 73/644

(58) Field of Classification Search
USPC ............................ 73/618, 620, 622, 629, 644
See application file for complete search history.

(56) References Cited

U.S. PATENT DOCUMENTS

| | | | |
|---|---|---|---|
| 4,156,228 A * | 5/1979 | Heckman | 367/173 |
| 4,304,133 A * | 12/1981 | Feamster, III | 73/633 |
| 4,375,818 A * | 3/1983 | Suwaki et al. | 600/463 |
| 4,848,159 A | 7/1989 | Kennedy et al. | |
| 5,398,216 A * | 3/1995 | Hall et al. | 367/90 |
| 5,485,751 A | 1/1996 | Karbach et al. | |
| 5,535,628 A | 7/1996 | Rutherford | |
| 5,623,107 A | 4/1997 | Patterson, Sr. et al. | |
| 7,464,596 B2 * | 12/2008 | Bui et al. | 73/618 |
| 7,516,664 B2 * | 4/2009 | Meier et al. | 73/644 |
| 7,640,811 B2 * | 1/2010 | Kennedy et al. | 73/634 |
| 7,703,327 B2 * | 4/2010 | Georgeson et al. | 73/624 |
| 8,371,173 B1 * | 2/2013 | DiMambro et al. | 73/629 |
| 2004/0016299 A1 | 1/2004 | Glascock et al. | |
| 2006/0027022 A1 | 2/2006 | Flora et al. | |
| 2007/0227249 A1 | 10/2007 | Meier et al. | |

FOREIGN PATENT DOCUMENTS

| | | |
|---|---|---|
| EP | 0 577 965 | 1/1994 |
| JP | 62-30951 | 2/1987 |
| RU | 1829928 | 7/1993 |
| SU | 1223137 | 4/1986 |

OTHER PUBLICATIONS

International Search Report for PCT/GB2008/050622, mailed Jul. 20, 2009.
Written Opinion of the International Searching Authority for PCT/GB2008/050622, mailed Jul. 20, 2009.
Chinese Office Action issued Apr. 27, 2012 in CN 200880130487.8.
Russian Office Action issued Feb. 28, 2012 in RU 2011104430/28(006240).
I.N. Ermolov et al, "Ultrasonic Inspection of Metals" 1957, pp. 9-11.
Panametrics catalog http://www.pts.cz/download/panametrics/en_transducer_catalog.pdf, May 2005.

* cited by examiner

*Primary Examiner* — J M Saint Surin
(74) *Attorney, Agent, or Firm* — Nixon & Vanderhye P.C.

(57) ABSTRACT

An ultrasound scanner (100) which has a plurality of ultrasound transducers (104) directed normal to a scanning surface (106) to scan a workpiece (114), the scanner (100) comprising a couplant filled latex rubber sheath (106) shaped to the surface of a workpiece (114).

21 Claims, 6 Drawing Sheets

INSPECTION DEVICE

This application is the U.S. national phase of International Application No. PCT/GB2008/050622 filed 24 Jul. 2008, which designated the U.S. and the entire contents of which is hereby incorporated by reference.

FIELD OF THE INVENTION

The present invention is concerned with a scanner. More specifically, the present invention is concerned with an ultrasonic testing (UT) scanner for non-destructive testing of metal and composite structures etc.

BACKGROUND OF THE INVENTION

Non-visible areas of materials, such as the interiors of components, welds and composite materials can be analysed using ultrasonic testing. This type of non-destructive testing (NDT) utilises the reflection of sound waves to detect faults and features which would otherwise be very difficult to detect without destroying the component in the process. Ultrasonic testing is a common technique in the aerospace sector to test the integrity of materials at manufacture and during service.

Scanners tend to be of the portable type (i.e. more suited to in-service scanning) or non-portable type (specifically for production).

A feature of ultrasonic testing is that a couplant is required to aid transmission of the ultrasonic energy to the test specimen because the acoustic impedance mismatch between air and solids (i.e. such as the test specimen) is large. This causes reflection of the sound waves and a loss in scan quality if a couplant is not used. Couplants generally take the form of water or gel or a deformable solid.

Traditionally, ultrasonic testing has been limited in terms of inspection speed as the operation had to be carried out on a point-by-point basis. Improvements have led to the development of array scanning, or "paintbrush" scanning which permits a continuous scan over a surface to produce a two dimensional image of the desired region of the test component. Such equipment however is bulky and limited to use in a production (as opposed to service) environment and is not considered portable.

Scanning of radii and tightly curved areas is a problem. Defects in e.g. laminar composites often occur parallel to the surface of the workpiece. As such the ultrasonic transducer needs to have its scanning vector oriented normal to the surface of the workpiece to scan effectively.

This causes problems in tightly curved areas, and especially at tight fillet radii found for example at the root of a stringer web. Such radii are in the order of 5 mm radius and the use of traditional bulky scanners in this area is not effective. In particular, linear scanning arrays can not project ultrasonic energy normal to the surface of a curved component.

It is desirable to scan such radii at a minimum resolution of about 1 mm.

It is an aim of the invention to provide an improved inspection device.

SUMMARY OF THE INVENTION

According to a first aspect of the invention there is provided an ultrasonic scanner for scanning a contoured workpiece, the scanner comprising:
a body,
a first ultrasound transducer having a first scanning direction,
a second ultrasound transducer having a second scanning direction, and,
a coupling component, the coupling component being configured to ultrasonically couple the transducers to the workpiece at a coupling surface,
in which the transducers are mounted to the body such that the first and second scanning directions are substantially perpendicular to the coupling surface and the first and second scanning directions are at a non-zero angle to each other.

Preferably the coupling surface is generally prismatic.

The coupling surface can comprise a fillet radius between two substantially planar surfaces. The planar surfaces can be substantially at right angles.

Preferably the coupling component comprises a deformable membrane defining a cavity for receiving a couplant liquid. Preferably the membrane is constructed from a latex rubber. Preferably the ultrasonic scanner comprises a couplant valve in fluid communication with the cavity for selective introduction and removal of the couplant liquid.

Alternatively the coupling component is constructed from a solid couplant material.

The plurality of ultrasonic transducers can be formed as a unitary ultrasonic scanning array.

Preferably the transducers are discrete ultrasonic transducers individually mounted to the body.

Preferably the transducers are mounted to the body such that the scanning directions each pass substantially through a single focal axis, and in which each scanning direction is perpendicular to the focal axis. The transducers can be mounted to the body such that the scanning vectors each pass substantially through a single focal point. The coupling surface can comprise a fillet radius and the focal axis is positioned substantially at the origin of the fillet radius. The fillet radius can be convex.

Preferably there is provided a liquid couplant delivery system configured to introduce liquid couplant to the coupling surface during scanning.

Preferably there is provided a roller element positioned to contact a surface of a workpiece during scanning.

Preferably the ultrasonic scanner comprises a first rotary encoder mounted to a first side of the body and positioned to contact a workpiece and measure movement of the scanner relative thereto during scanning.

Preferably the ultrasonic scanner comprises a second rotary encoder mounted to a second side of the body substantially opposite the first side and positioned to contact a workpiece and measure movement of the scanner relative thereto during scanning.

Preferably the coupling component is replaceable.

Preferably the coupling component is retained between a first body component and a second body component and the first body component and the second body component are joined by a snap fit.

According to a second aspect of the invention there is provided a scanning assembly for scanning a workpiece, the assembly comprising a body, a plurality of ultrasound transducers each having a scanning vector, in which the transducers are mounted to the body such that the scanning vectors pass substantially through a single focal axis and each of the scanning vectors is substantially perpendicular to the focal axis.

Preferably the transducers are mounted to the body such that the scanning vectors each pass substantially through a single focal point.

According to a third aspect of the invention there is provided a method of ultrasonically scanning a surface of a workpiece comprising the steps of:

provide a workpiece to be scanned, providing a scanning device comprising a first ultrasound transducer having a first scanning vector aligned with a first plane, and a second ultrasound transducer having a second scanning vector aligned with a second plane parallel but offset to the first plane in a scanning direction, moving the scanner to align the first plane with a scanning plane intersecting the workpiece at a scan line, scanning a first position on the scan line with the first ultrasound transducer, moving the scanner to align the second plane with the scanning plane, scanning a second position on the scan line with the first ultrasound transducer, combining the results of the first and second scanning steps to produce an image of a part of the scan line.

Preferably the step of providing a scanning device comprises the step of:

providing a scanning device comprising a first plurality of ultrasound transducers having a plurality of first scanning vectors aligned with the first plane, and a second plurality of ultrasound transducers having a plurality of second scanning vectors aligned with the second plane, the step of scanning a first position comprises the step of scanning a plurality of first positions, and;

the step of scanning a second position comprises the step of scanning a plurality of second positions.

BRIEF DESCRIPTION OF THE DRAWINGS

FIG. 3b shows a perspective view of a part of the scanning device of FIG. 3a, and FIG. 3c shows a perspective view of another part of the scanning device of FIG. 3a,

DETAILED DESCRIPTION OF THE PREFERRED EMBODIMENT

Figure 1A:
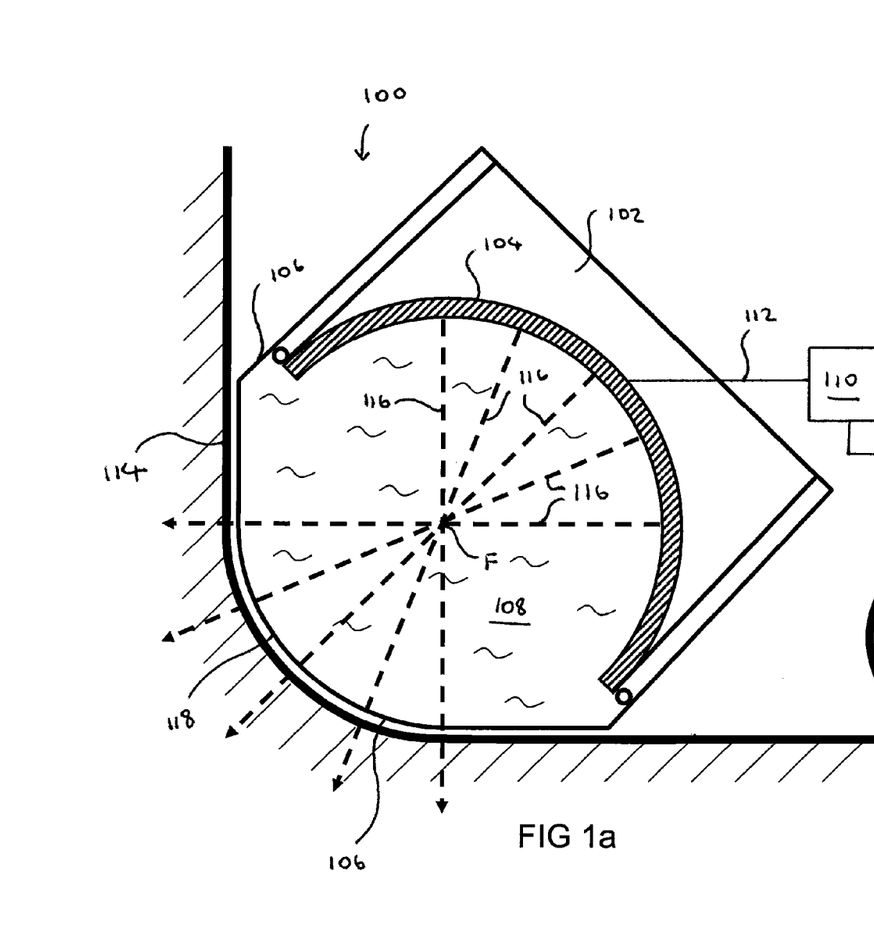
FIG. 1a is a side section view along line A-A of FIG. 1b of a first scanning device in accordance with the present invention.
Figure 1B:
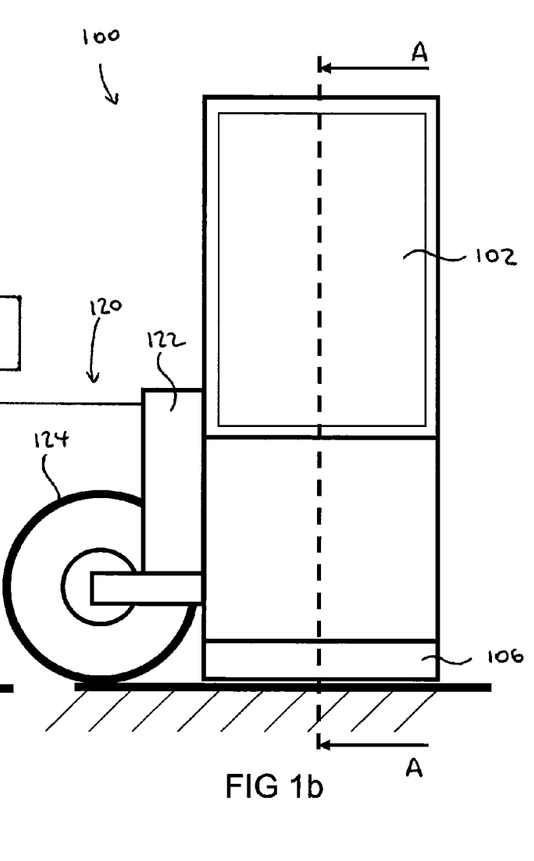
FIG. 1b is a rear view of the scanning device of FIG. 1a, FIG. 2a shows a perspective view of a second scanning device in accordance with the present invention.

Referring to FIGS. 1a and 1b, there is provided a scanning device 100 comprising a body 102 housing an ultrasonic scanning array 104. The device 100 further comprises a latex rubber boot 106 connected to the body 102 and enclosing the array 104. The boot 106 is filled with a couplant liquid 108.

The array 104 is arcuate in form and is connected to a computer 110 via a data connection 112. The array 104 is capable of transmitting and receiving ultrasonic energy for the non-destructive testing of a composite workpiece 114.

The array 104 emits ultrasonic energy perpendicular to its inner surface, as is shown by example vectors 116. The vectors 116 cross at a focal point F. The outer surface of the boot 106 is shaped in the form of an arc 118 with a geometric centre at the focal point F.

Turning to FIG. 1b, the device 100 further comprises a rotary encoder 120 comprising a frame 122 and an encoder wheel 124. The encoder wheel 124 is mounted such that it projects as far as the outer surface of the boot 106. The encoder wheel 124 is spring mounted. The encoder 120 is also connected to the computer 110. The encoder is capable of reporting the linear distance traveled by the device 100 along the workpiece 114.

In use, the device 100 is positioned proximate a filleted area of the workpiece 114 such that the boot 106 fits within the filleted area. The boot 106 is selected to be of a comparable or identical shape to the workpiece 114.

As the focal point F is positioned at the centre of the arc 118 of the boot, it is also positioned at the centre of the arc of the workpiece 114. As such, the vectors 116 are perpendicular to the surface of the workpiece 114. This is the optimum orientation for detecting faults in the workpiece that are parallel to its surface—for example delamination in composite materials.

Figure 2A:
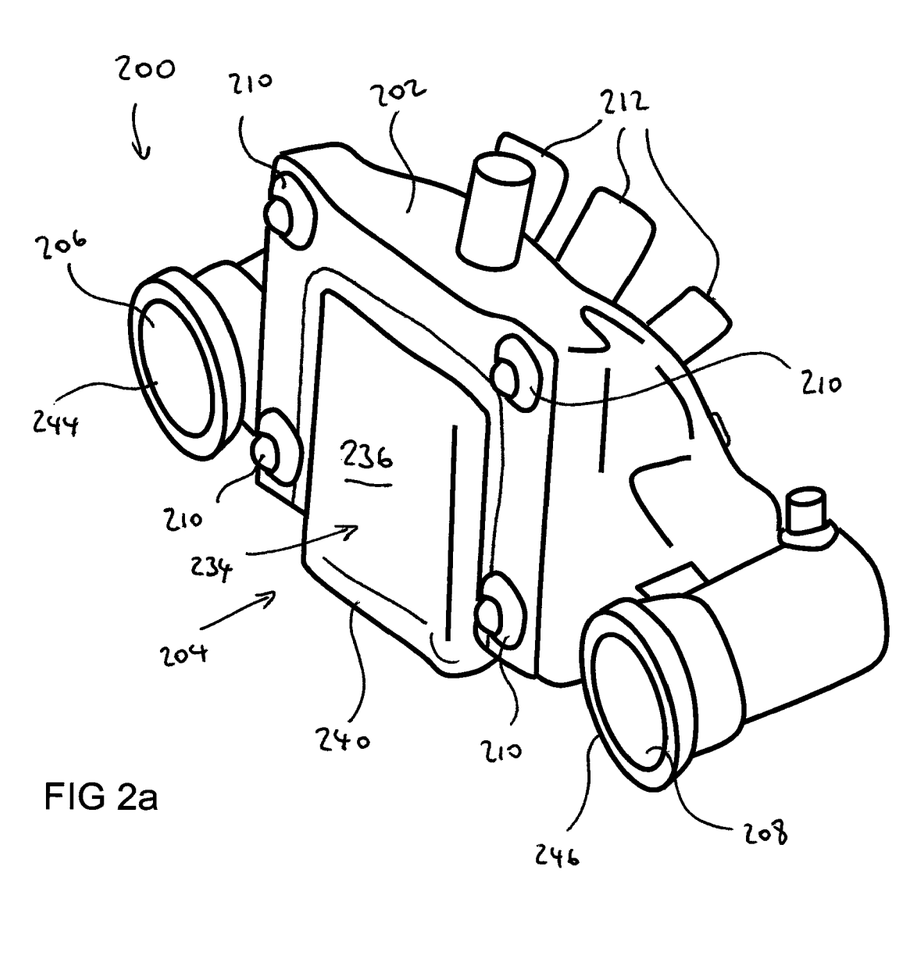
Figure 2B:
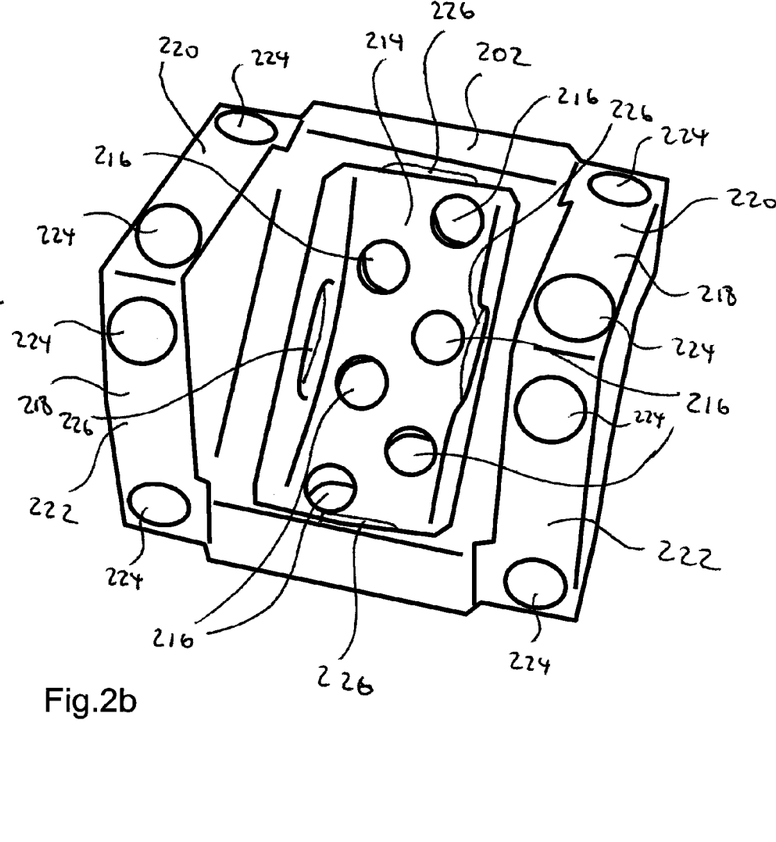
FIG. 2b shows a perspective view of a part of the scanning device of FIG. 2a, FIG. 2c shows a schematic side section view of the scanning device of FIG. 2a, FIG. 2d shows a schematic perspective view of a part of the scanning device of FIG. 2a, FIG. 3a shows a perspective view of a third scanning device in accordance with the present invention.

Turning to FIGS. 2a and 2b, a scanning device 200 is shown. The device 200 comprises a housing 202, a coupling assembly 204, a first encoder 206, a second encoder 208, runners 210 and a plurality of ultrasound transducers 212.

The interior of the housing 202 is shown in more detail in FIG. 2b. The housing comprises an arcuate portion 214 with a series of through bores 216 formed therethrough. The through bores 216 are arranged as two offset rows in the arcuate portion.

The housing 202 comprises a pair of wings 218 each comprising a pair of faces 220, 222 positioned at right angles to each other. The faces 220, 222 each have a pair of recesses 224 defined therein.

The housing 202 defines four tab receiving portions 226 surrounding the arcuate portion 214.

The coupling assembly 204 is also shown in more detail in FIG. 2b. The coupling assembly 204 comprises a frame part 228 defining a rectangular through bore 230. Four tabs 232 are positioned on the sides of the bore 230.

A latex rubber sheath 234 is attached and sealed to the periphery of the frame part 228. The sheath 234 comprises a rectangular front face 236, a rectangular base face 238 at right angles to the front face 236, and a fillet radius 240 positioned therebetween. The sheath 234 comprises triangular side faces 242 and is sealed to the frame part to enclose a volume with a single open face at the bore 230 of the frame part 228.

Figure 2C:
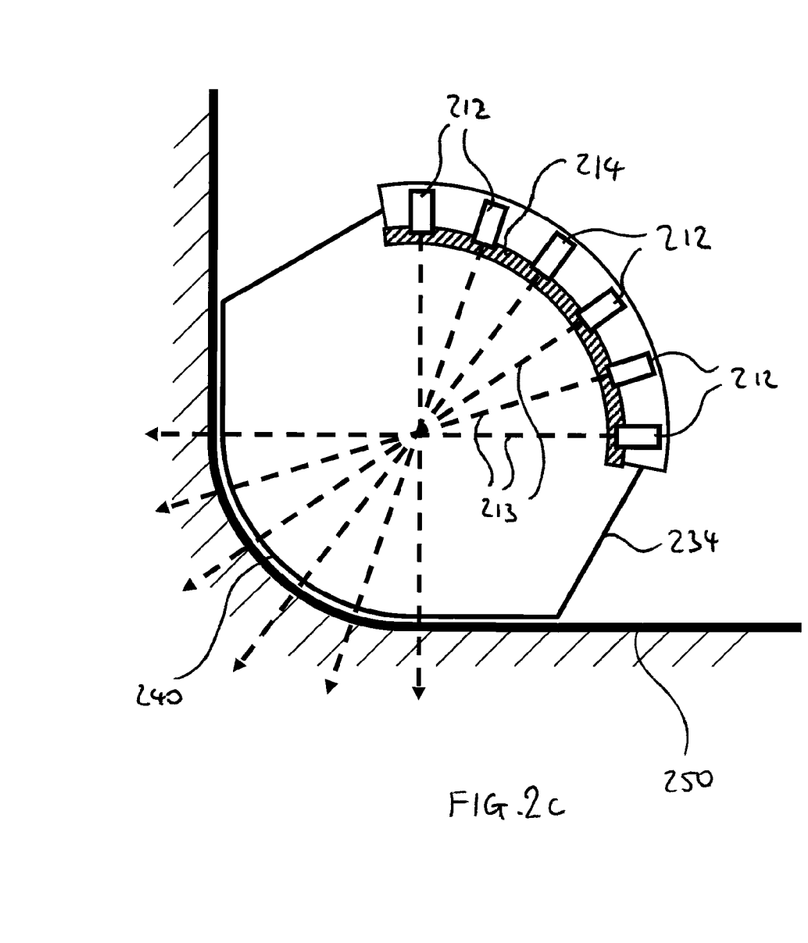
Figure 2D:
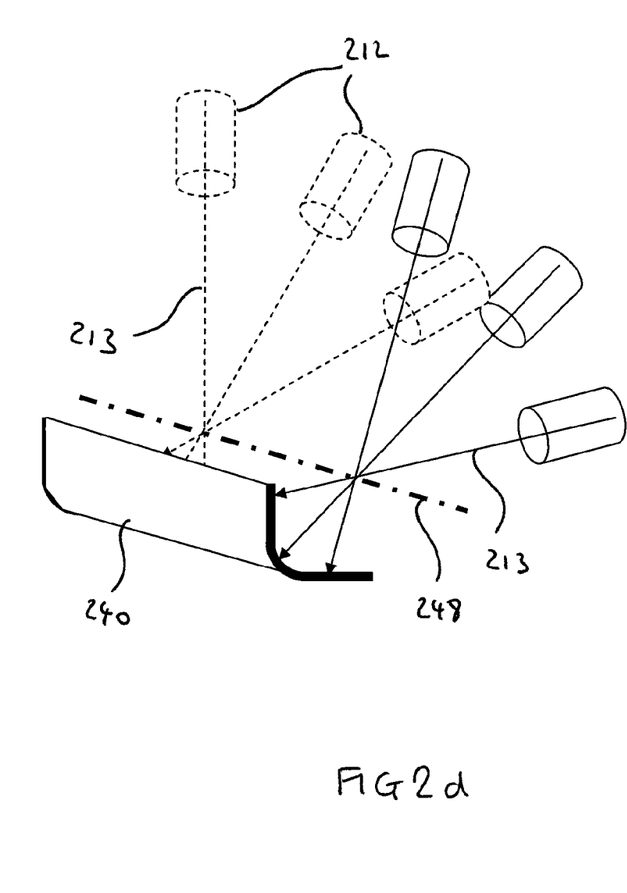

The first and second encoders 206, 208 are rotary encoders with encoder wheels 244, 246 respectively The ultrasound transducers 212 are inserted into each of the bores 216. As such, they are positioned in an arcuate fashion. Referring to FIG. 2c the arcuate formation of the transducers 212 is shown. As can be seen in FIGS. 2c and 2d, the scanning directions 213 of each transducer 212 intersect a focal axis 248. Referring to FIG. 2d, each row of transducers 212 intersects the focal axis 248 at a different position.

Placing the transducers in rows is advantageous as more transducers can be incorporated into the device. Single transducers are less expensive than arrays and as such using several single transducers is more economical than a curved array.

No two transducers have parallel scan directions—as such the results from each row are unique and can be combined with each other to produce a higher resolution image.

Further, the scanning directions 213 of each transducer 212 intersects the outer surface of the sheath 234 normal to that surface, i.e. the centre of the fillet radius 240 is coincident with the focal axis 248.

The runners 210 are simple ball bearing runners and are mounted into the recesses 224 in the housing 202.

The coupling assembly 204 is assembled to the housing 202 by inserting the tabs 232 into the tab receiving portions 226. The tabs 232 and the portions 226 engage to form a snap fit. The sheath can then be filled with couplant liquid (in this case water) through one of the bores 216 by removing a transducer or via a customised fill valve (not shown).

In use, the device 200 is engaged with a curved part 250 to be scanned. The transducers are used to scan the part 250 whilst the device 200 is slid along in the direction of the focal axis 248. The encoders 206, 208 record the distance traveled such that an image of the part 250 is formed.

It should be noted that by using a pair of encoders disposed at either end of the device 200, scanning can be completed to the edge of a component even if one of the encoders loses contact with the surface being scanned. The distance traveled can simply be recorded by the one encoder still in contact with the surface.

It should also be noted that due to the clip-in nature of the frame 228, the sheath 234 is easily replaceable.

Figure 3A:
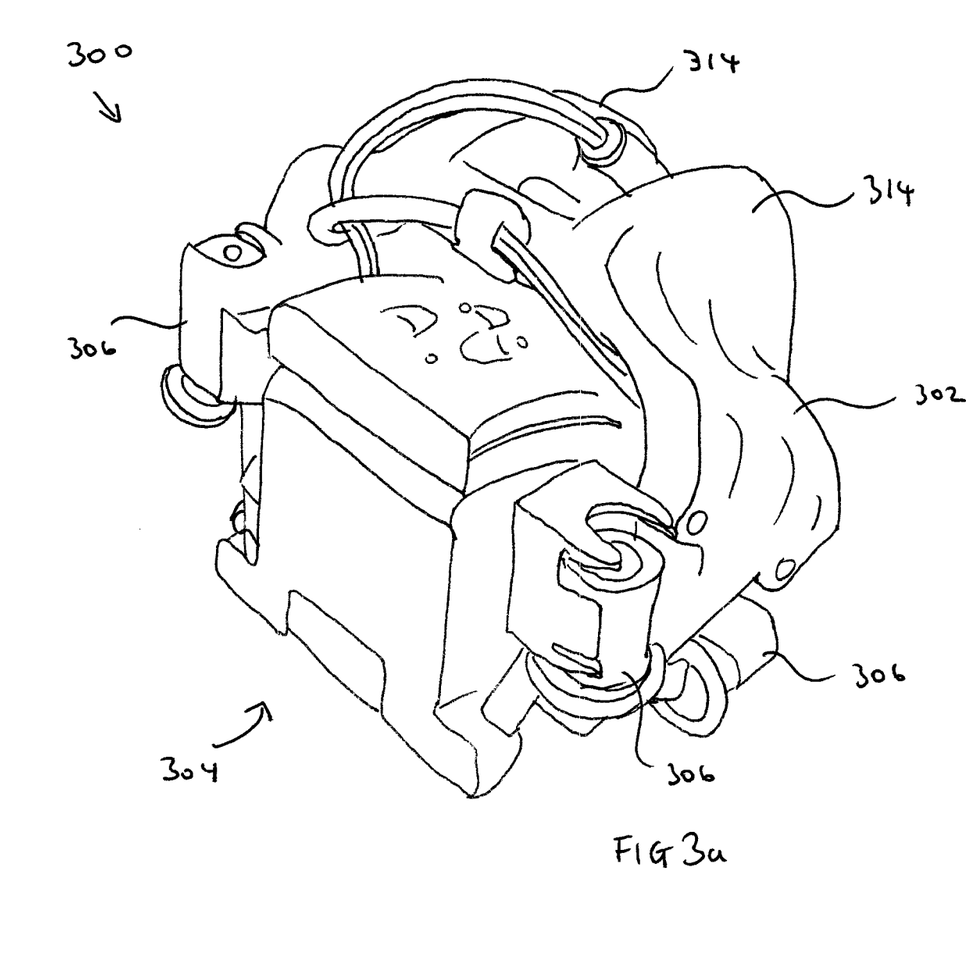
Figure 3B:
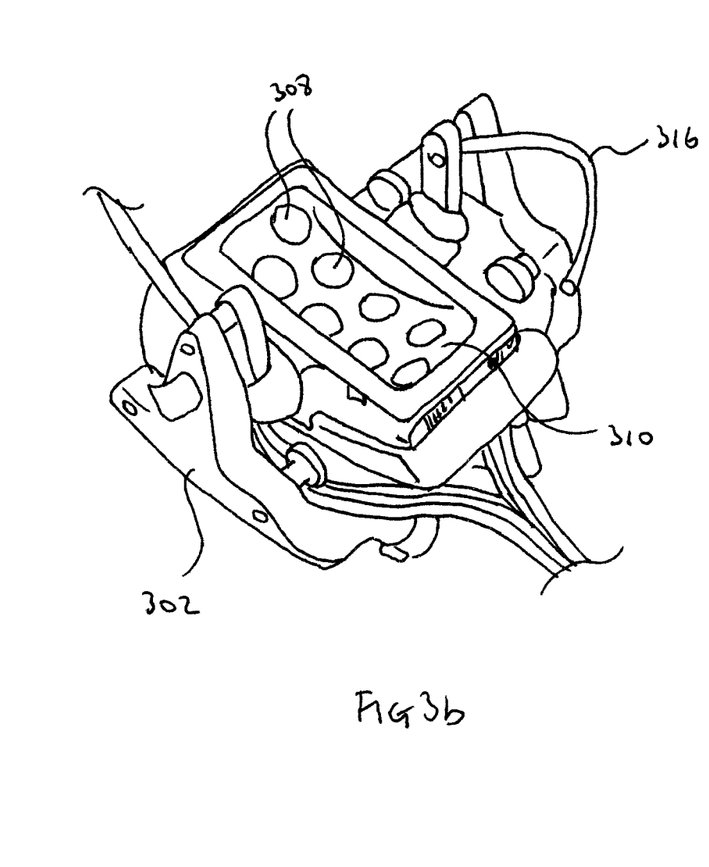
Figure 3C:
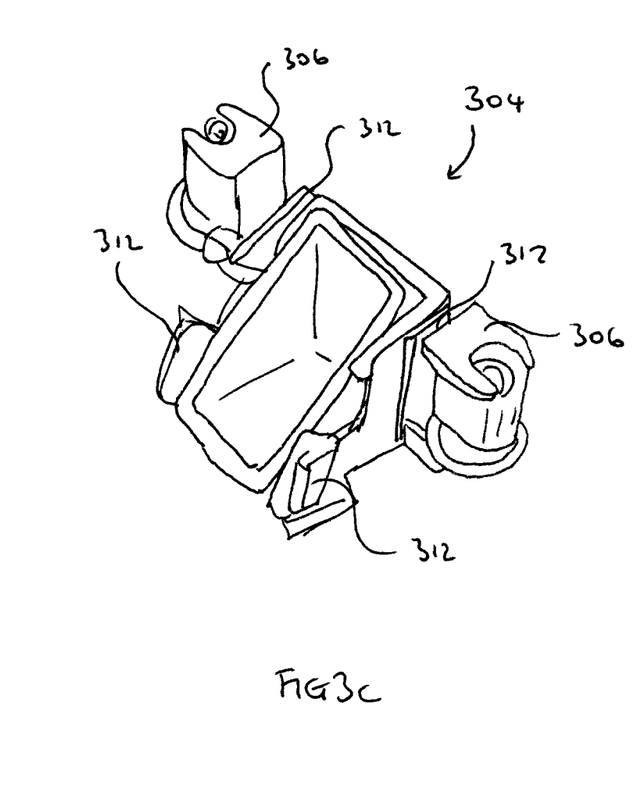

FIGS. 3a to 3c show a scanning device 300 comprising a housing 302, a coupling assembly 304, eight ultrasonic transducers (not shown) and four rotary encoders 306.

The basic structure of the device 300 is similar to that of the device 200. In the device 300, the housing 302 comprises eight bores 308 defined on an arcuate portion 310.

The coupling assembly 304 comprises four encoder mounts 312 on which encoders 306 are mounted. It should also be noted that the encoders 306 are oriented such that they can contact both a flange and a root of a part to be inspected. The encoders are positioned on either side of the housing 302 as per device 200. As such, the reliability and accuracy of the encoding process is improved.

The housing 302 is constructed from a moulded plastics material and comprises a pair of ribs 314 projecting therefrom to allow a user to grip the housing 302 and slide the device 300 along the part to be inspected.

Further, a couplant supply conduit 316 is provided to supply couplant to the surface of the coupling assembly 304. This improves the ultrasonic coupling during use.

Providing two rows of transducers as shown in devices 200 and 300 causes problems in that if all of the transducers scan at a given distance traveled (say, 1 mm intervals), the image slice produced by the transducers is distorted as they are not aligned. This can be remedied by:

Detecting a desired movement distance of the scanner along the workpiece,

Scanning using the leading (i.e. forward) set of transducers,

Detecting a further movement of the scanner equal to the distance between the leading and trailing (i.e. rearward) set of transducers, Scanning using the trailing (i.e. rearward) set of transducers.

When presenting the information, the results produced by the trailing set is regarded as if it was produced simultaneously with the leading set.

Another method of solving this problem is to offset the results from one of the sets of transducers by a distance equal to the distance between the sets. This step may be completed by post processing software.

Variations of the above embodiments fall within the scope of the present invention.

For example, any number of transducers may be used.

Additionally, further rows of transducers may be used to improve coverage.

The coupling surface need not be a pair of planar surfaces connected by a convex fillet radius, and can be any non-planar profile suited to the profile of the workpiece—for example curved, arcuate, undulating (corrugated) or angled (V-section).

The invention claimed is:

1. An ultrasonic scanner for scanning a contoured workpiece, the scanner comprising:
   a body,
   a first ultrasound transducer having a first scanning direction,
   a second ultrasound transducer having a second scanning direction, and,
   a coupling component with a coupling surface, the coupling component configured to ultrasonically couple the transducers to the workpiece at said coupling surface,
   wherein the transducers are mounted to the body with the first and second scanning directions substantially perpendicular to the coupling surface, the first and second scanning directions are at a non-zero angle to each other, the scanning directions pass perpendicular to and substantially through a single focal axis, said focal axis located between the transducers and the coupling surface.

2. An ultrasonic scanner according to claim 1 in which the coupling surface is generally prismatic.

3. An ultrasonic scanner according to claim 2 in which the coupling surface comprises a fillet radius between two substantially planar surfaces.

4. An ultrasonic scanner according to claim 3 in which the planar surfaces are substantially at right angles.

5. An ultrasonic scanner according to claim 1 in which the coupling component comprises a deformable membrane defining a cavity for receiving a couplant liquid.

6. An ultrasonic scanner according to claim 5 in which the membrane is constructed from a latex rubber.

7. An ultrasonic scanner according to claim 5 comprising a couplant valve in fluid communication with the cavity for selective introduction and removal of the couplant liquid.

8. An ultrasonic scanner according to claim 1 in which the coupling component is constructed from a solid couplant material.

9. An ultrasonic scanner according to claim 1 in which the plurality of ultrasonic transducers are formed as a unitary ultrasonic scanning array.

10. An ultrasonic scanner according to claim 1 in which the transducers are discrete ultrasonic transducers individually mounted to the body.

11. An ultrasonic scanner according to claim 1 in which the transducers are mounted to the body such that the scanning vectors each pass substantially through a single focal point.

12. An ultrasonic scanner according to claim 1 in which the coupling surface comprises a fillet radius and the focal axis is positioned substantially at the origin of the fillet radius.

13. An ultrasonic scanner according to claim 12 in which the fillet radius is convex.

14. An ultrasonic scanner according to claim 1 comprising a liquid couplant delivery system configured to introduce liquid couplant to the coupling surface during scanning.

15. An ultrasonic scanner according to claim 1 comprising a roller element positioned to contact a surface of a workpiece during scanning.

16. An ultrasonic scanner according to claim 1 comprising a first rotary encoder mounted to a first side of the body and positioned to contact a workpiece and measure movement of the scanner relative thereto during scanning.

17. An ultrasonic scanner according to claim 16 comprising a second rotary encoder mounted to a second side of the body substantially opposite the first side and positioned to contact a workpiece and measure movement of the scanner relative thereto during scanning.

18. An ultrasonic scanner according to claim 1 in which the coupling component is replaceable.

19. An ultrasonic scanner according to claim 1 in which the coupling component is retained between a first body component and a second body component and the first body component and the second body component are joined by a snap fit.

20. A method of ultrasonically scanning a surface of a workpiece comprising the steps of:
provining a workpiece to be scanned,
providing a scanning device comprising a first ultrasound transducer having a first scanning vector aligned with a first plane, and a second ultrasound transducer having a second scanning vector aligned with a second plane parallel but offset to the first plane in a scanning direction,
moving the scanner to align the first plane with a scanning plane intersecting the workpiece at a scan line,
scanning a first position on the scan line with the first ultrasound transducer,
moving the scanner to align the second plane with the scanning plane,
scanning a second position on the scan line with the first ultrasound transducer,
combining the results of the first and second scanning steps to produce an image of a part of the scan line.

21. A method of ultrasonically scanning a surface of a workpiece according to claim 20 in which the step of providing a scanning device comprises the step of:
providing a scanning device comprising a first plurality of ultrasound transducers having a plurality of first scanning vectors aligned with the first plane, and a second plurality of ultrasound transducers having a plurality of second scanning vectors aligned with the second plane,
the step of scanning a first position comprises the step of scanning a plurality of first positions, and;
the step of scanning a second position comprises the step of scanning a plurality of second positions.

* * * * *